United States Patent [19]
Tsai

[11] Patent Number: 5,394,980
[45] Date of Patent: Mar. 7, 1995

[54] MULTICOMPARTMENT MIXING CAPSULE

[76] Inventor: Min H. Tsai, 14912 Gilmore St., Van Nuys, Calif. 91411

[21] Appl. No.: 173,712

[22] Filed: Dec. 23, 1993

Related U.S. Application Data

[63] Continuation of Ser. No. 46,375, Apr. 7, 1993, abandoned, which is a continuation of Ser. No. 798,875, Nov. 25, 1991, abandoned, which is a continuation of Ser. No. 669,203, Mar. 14, 1991, abandoned, which is a continuation of Ser. No. 567,682, Aug. 14, 1990, abandoned, which is a continuation of Ser. No. 449,361, Dec. 6, 1989, abandoned, which is a continuation of Ser. No. 317,141, Mar. 1, 1989, abandoned, which is a continuation of Ser. No. 68,124, Jun. 30, 1987, abandoned.

[51] Int. Cl.$^6$ .............................................. A61B 19/02
[52] U.S. Cl. .................................. 206/63.5; 206/219; 206/222; 215/DIG. 8
[58] Field of Search ............... 206/219, 220, 221, 222, 206/368, 63.5; 220/281; 215/250, DIG. 8

[56] References Cited

U.S. PATENT DOCUMENTS

| | | |
|---|---|---|
| 2,773,591 | 12/1956 | Jensen . |
| 3,216,611 | 11/1965 | Lechevallier . |
| 3,489,306 | 1/1970 | Bubb . |
| 3,809,225 | 5/1974 | Allet-Coche ........................ 206/220 |
| 3,963,120 | 6/1976 | Perfect ................................ 206/219 |
| 4,136,775 | 1/1979 | Zaltsman ........................... 206/219 |
| 4,182,447 | 1/1989 | Kay ..................................... 206/220 |
| 4,185,740 | 1/1980 | Perfect ................................ 206/220 |
| 4,197,943 | 4/1980 | Weikel ................................. 206/219 |
| 4,362,242 | 12/1982 | Cheetham .......................... 206/219 |
| 4,552,266 | 11/1985 | Weissenburger .................. 206/220 |

Primary Examiner—David T. Fidei
Attorney, Agent, or Firm—Christie, Parker & Hale

[57] ABSTRACT

A multicompartment mixing capsule which is particularly useful for storage and subsequent intermixing of mercury and silver or a silver alloy to form a dental amalgam material. The amalgam components are contained in separate capsule chambers which are insulated by a diaphragm having a thin frangible perimeter, and a thickened and strengthened center portion. A pestle in one of the chambers impacts the diaphragm during initial capsule shaking in an amalgamator to rupture the frangible diaphragm perimeter, and thereby to permit complete and unimpeded intermixing of the amalgam components.

12 Claims, 1 Drawing Sheet

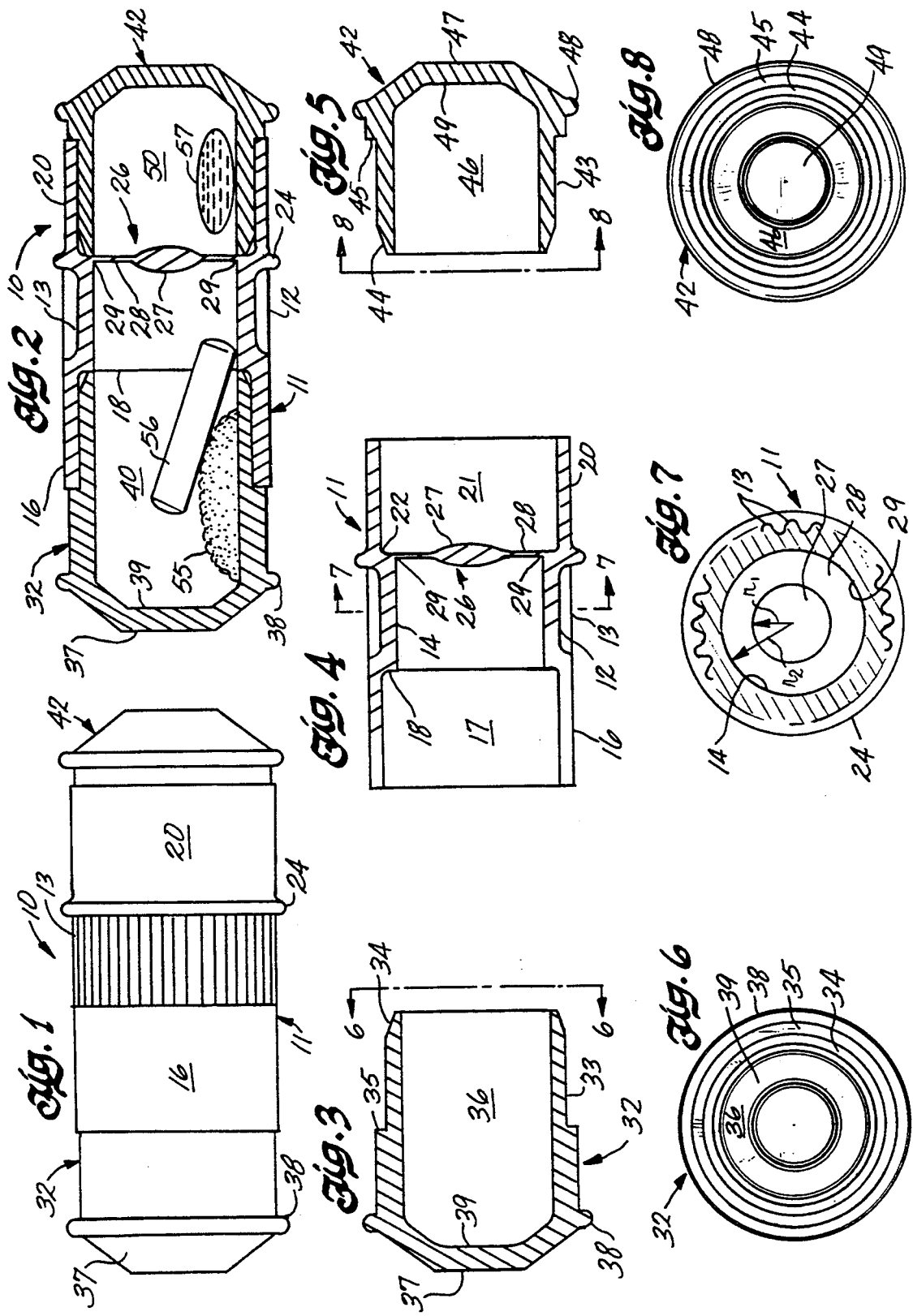

MULTICOMPARTMENT MIXING CAPSULE

This is a continuation of application Ser. No. 08/046,375, filed on Apr. 7, 1993, now abandoned; which is a continuation of Ser. No. 07/798,875, filed Nov. 25, 1991, now abandoned; which is a continuation of Ser. No. 07/669,203, filed Aug. 14, 1990, now abandoned; which is a continuation of Ser. No. 07/449,361, filed Dec. 6, 1989, now abandoned; which is a continuation of Ser. No. 07/317,141, filed Mar. 1, 1989, now abandoned; which is a continuation of Ser. No. 07/068,124, filed Jun. 30, 1987, now abandoned.

BACKGROUND OF THE INVENTION

Amalgam materials for filling a prepared tooth cavity are well known in dentistry, and are formulated by vigorous mixing or triturating of mercury and a powder or pellet of silver or silver alloy. The resulting amalgam is temporarily viscous and formable so it can be packed into the tooth cavity. The amalgam sets quickly to a hard and wear-resistant restoration of the lost tooth structure.

It was common many years ago for a dentist or assistant to measure the individual amalgam components, and to mix the components manually immediately before packing into the cavity. This time-consuming and error-prone procedure (which involves handling of mercury) is replaced in modern dentistry by factory prepackaging of the isolated and precisely measured components in a multicompartment capsule or container. The capsule is manipulated to enable the components to flow together and mix when the capsule is inserted into a high-speed vibratory shaker or amalgamator. The capsule is then separated so the resulting amalgam can be dispensed.

Prior to the mixing procedure, it is essential that the mercury and silver components be completely isolated from each other by a barrier, but it is also desirable to have a quick and simple way of enabling the components to intermix completely when the capsule is shaken. In some capsule designs, the capsule is manipulated (e.g., by twisting of an end portion, or depression of a plunger) to puncture, sever or dislodge the barrier. Other designs are intended for automatic puncture or separation of the barrier by impact of a pestle (a rod or bar within one of the capsule compartments, and which aids the mixing process) during initial shaking of the capsule on an amalgamator. Summaries of typical such prior-art capsules are given in U.S. Pat. Nos. 4,182,447 and 4,552,266 and, for brevity, will not here be repeated.

The goal of good capsule design is to provide a leak-free multicompartment container which stores the components in complete isolation, and yet insures complete intermixing with as little handling as possible by the dentist or technician. Capsules which require twisting or plunger activation require extra handling and careful manipulation, and the interior separation-barrier parts tend to diminish the available mixing volume which should be large (with respect to the volume of the mercury and silver-alloy powder or pellet) to insure fast and thorough component mixing. So-called "automatic" capsules (having amalgamator-initiated barrier separation) have also proved to be unreliable, the most common problems being complete failure of barrier release or separation, or partial failure such as incomplete rupture or puncture of a constant-thickness barrier diaphragm which prevents proper component intermixing.

The capsule of this invention is a significant forward step in the design of multicompartment containers, and is an "automatic" design which need only be placed in a shaker or amalgamator for the desired mixing interval, and then removed and separated to dispense the amalgam. No premixing manipulation of the capsule is needed, and a novel internal barrier diaphragm is reliably and completely opened during initial capsule shaking to enable thorough component mixing in a large, unimpeded chamber.

SUMMARY OF THE INVENTION

This invention is directed to a multicompartment capsule which has particular utility in the storage and eventual intermixing of dental amalgam components. The capsule is a three-part assembly having a hollow central body which is closed at opposite ends by a pair of end caps press fitted into the body. The central body has an internal diaphragm which defines with the end caps a pair of sealed chambers or compartments for holding the amalgam components (mercury, and silver or silver alloy) and a pestle.

The central-body diaphragm is integrally formed to extend across a bore or passage in the body, and has a thin and frangible perimeter at its junction with the body. The more central part of the diaphragm is strengthened by having a thick cross section relative to the frangible perimeter. When the capsule is vigorously shaken along its axial dimension perpendicular to the plane of the diaphragm, pestle impact effects rupture of the diaphragm perimeter and separation of the diaphragm to enable intimate and complete intermixing of the amalgam components.

BRIEF DESCRIPTION OF THE DRAWINGS

FIG. 1 is a side elevation of a capsule according to the invention;

FIG. 2 is a sectional side elevation of the capsule;

FIG. 3 is a sectional side elevation of a first end cap;

FIG. 4 is a sectional side elevation of a central tubular body of the capsule;

FIG. 5 is a sectional side elevation of a second end cap;

FIG. 6 is an end view on line 6—6 of FIG. 3;

FIG. 7 is an axial sectional view on line 7—7 of FIG. 4; and

FIG. 8 is an end view on line 8—8 of FIG. 5.

DETAILED DESCRIPTION OF THE PREFERRED EMBODIMENT

A three-part capsule 10 is shown in FIGS. 1 and 2, and an integrally molded center section or central tubular body 11 of the capsule is further shown in FIGS. 4 and 7. Body 11 is cylindrical in cross section, and has a tubular center portion 12 with external gripping ribs 13, and an internal bore 14. A first sleeve 16 extends (to the left in FIGS. 2 and 4) from one end of the center portion, and defines an internal bore 17 slightly larger in diameter than bore 14 to define an annular shoulder 18. A second sleeve 20 extends (to the right in FIGS. 2 and 4) from the opposite end of the center portion, and defines an internal bore 21 which is also slightly larger in diameter than bore 14 to define another annular shoulder 22.

The outside diameter of center portion 12 is substantially constant (apart from the depressions between ribs 13), and is interrupted only by an outwardly extending annular gripping rib 24 which is coaxial with the cylindrical axis of the center portion, and axially positioned adjacent annular shoulder 22. A thin integrally formed diaphragm 26 extends across bore 14 of the center portion at shoulder 22 to isolate and seal bores 17 and 21 from each other.

A central portion 27 of diaphragm 26 is substantially increased in thickness (about seven-fold) as compared to a thin and annular radially outer diaphragm portion 28 which is integrally joined at its perimeter 29 to the inner surface of tubular center portion 12 immediately adjacent shoulder 22. The intersection of perimeter 29 with the inner surface of portion 12 is made as close as possible to a right angle, thereby minimizing perimeter thickness to make the radially outermost part of the diaphragm frangible as described below.

A first end cap 32 (FIGS. 1–3 and 6) is integrally molded and cylindrical in cross section, and defines a sleeve 33 dimensioned to make a snug press fit in bore 17 of central body 11. An inner end 34 of sleeve 33 is inwardly tapered to enable easy insertion into the central body. Sleeve 33 is enlarged in outside diameter midway along its axial length to form an annular shoulder 35 which abuts the end of sleeve 16 of the central body (FIG. 2) when the parts are fully seated.

End cap 32 has a blind internal bore 36 (of diameter matching that of bore 17) which is closed at its outer end by an end wall 37 having an annular gripping rib 38 extending radially outward from its outer surface. An inner surface 39 of the end wall is dished to avoid crevices which might trap silver-alloy powder or otherwise interfere with efficient mercury-powder intermixing. Bores 17 and 36 extend smoothly between diaphragm 26 and end wall 37 to define a first chamber 40 (FIG. 2).

A second end cap 42 (FIGS. 1–2, 5 and 8) is axially shorter than, but otherwise generally similar in configuration to first cap 32. Cap 42 thus has a sleeve 43 with a tapered inner end 44, an external annular shoulder 45 (which abuts shoulder 22 when the cap is fitted into the central body), a blind internal bore 46 (of matching diameter to bores 17 and 36), and an end wall 47 with an external annular gripping rib 48 and a dished inner surface 49. Bore 46 extends between diaphragm 26 and end wall 47 to define a second chamber 50 (FIG. 2).

For economy and ease of manufacture, the three components (central body 11, and end caps 32 and 42) are preferably injection molded in a plastic material. A presently preferred material for these three parts is polyethylene plastic which is well suited to close-tolerance injection molding. With the exception of the diaphragm perimeter which must have a thin cross section, the capsule dimensions are not critical, and nominal values (in inches) are as follows:

| | |
|---|---|
| Overall assembled length | 1.31 |
| Outside body diameter | 0.47 |
| Gripping rib diameter | 0.52 |
| Mixing chamber diameter | 0.34 |
| First end cap length | 0.60 |
| Second end cap length | 0.44 |
| Depth of axial ribs | 0.06 |
| Diaphragm perimeter thickness | 0.006–0.007 |
| Diaphragm central thickness | 0.050 |
| Diameter of bulged central diaphragm | 0.16 |
| Diameter of chambers 40 and 50 | 0.34 |
| Axial length of first mixing chamber | 0.81 |
| Axial length of second mixing chamber | 0.39 |

First end cap 32 is removable from the capsule after the mixing operation in order to dispense the amalgam, and the cap sleeve portion which fits within central body 11 has an outside diameter about 0.002-inch larger than bore 17 to provide a snug but releasable interference fit. Second end cap 42 is normally not removed, and the sleeve portion which fits within central body 11 has an outside diameter about 0.010-inch larger than bore 21 for a hard interference fit which provides a positive seal for mercury within this cap. The sleeves can of course be of identical diameter, with the difference in interference fit being provided by slightly different internal diameters at the ends of central-body bores 17 and 21 on opposite sides of diaphragm 26.

In assembly, a controlled amount (in the range of 0.4 to 0.8 grams, and typically 0.6 grams) of a silver-alloy powder 55 (which may also be in compressed pellet or tablet form) is inserted within first end cap 32 as shown in FIG. 2, along with a rounded-end and rod-shaped steel pestle (a weight of about 0.7 grams is typical) 56 of about 0.7 inch length and 0.126-inch diameter. A rod-shaped pestle is presently preferred, but other pestle shapes such as a ball can be used.

The first cap is then pressed into the central body to trap the alloy and pestle in first chamber 40. A controlled volume of mercury 57 (typically about 0.045 cc) is dispensed into second end cap 42 which is then pressed into the central body to trap the mercury in second chamber 50. The assembled capsule is shipped by the amalgam manufacturer in this form, and is ready for use by the dentist.

When the mercury and alloy are to be mixed in preparation for forming a dental restoration or filling, the capsule is simply inserted in a conventional vibratory shaker or amalgamator of the style common in dental offices. Upon initiation of vigorous oscillatory shaking, pestle 56 impacts against diaphragm 26 to rupture the thin junction of diaphragm perimeter 29 with the inner surface of the central body. The severed diaphragm is driven to one end of the capsule interior (i.e., into end cap 42), permitting free intermixing of the alloy and mercury by the pestle in the unimpeded and now-joined chambers 40 and 50 which have a desirably large combined volume.

The function of thickened central portion 27 of the diaphragm is to strengthen this section against minor punctures or tears which would not allow adequate intermixing of the amalgam components, and to insure that diaphragm separation occurs at the outer edge or perimeter to provide a completely open passage between the first and second chambers. Tests have established that even an incomplete separation of the diaphragm perimeter will not impede efficient intermixing, because the unbroken portion of the perimeter permits the diaphragm to hinge against the chamber sidewall to provide the desired completely open passage between the first and second chambers.

When the mixing cycle (typically controlled by an adjustable automatic timer on the amalgamator) is complete, the capsule is gripped by ribs 13, and first end cap 32 is slipped or twisted out of the central capsule body so the amalgam can be dispensed. The capsule is so economical to make that it is treated as a single-use throw-away product which is discarded after amalgam mixing and dispensing.

As shown in FIG. 2, pestle 56 is packaged in first chamber 40 which is longer (by a factor of about two to one) than second chamber 50 which contains the mercury droplet. Chamber 40 is also substantially longer than the pestle, thereby enabling the pestle to acquire sufficient kinetic energy at the onset of amalgamator shaking to rupture the diaphragm perimeter for clean diaphragm separation.

There are several design features of diaphragm 26 which are important in maintaining isolation of the capsule contents during packaging, shipping and handling, while still insuring reliable diaphragm separation during amalgamation:

a. The radial dimension ($r_2-r_1$ in FIG. 8) of the thin and annular radially outer portion of the diaphragm must be sufficiently large (with respect to overall diaphragm radius $r_2$) to give this thin annulus sufficient radial elasticity to withstand the outward radial stress resulting from force (interference) fitting of the end caps into the central tubular body. A thin annular portion of very small radial dimension will rupture upon insertion of the end caps, and is unsuitable. An $r_2/r_1$ ratio of about 2 has been found to provide reliable capsule performance, and this ratio is preferably not less than 1.5.

b. Cross-sectional thickness of the thin diaphragm outer annulus is preferably about 0.006 to 0.007 inch as mentioned above, can be in the range of 0.004 to 0.012 inch. A very thin cross section presents molding problems when making the injection-molded plastic part, and a very thick cross section has sufficient strength to interfere with diaphragm separation during capsule shaking.

c. The thickened central diaphragm portion should have a diameter which is larger than the cross section of the pestle to avoid unwanted puncture of the diaphragm, and to achieve complete diaphragm separation by rupture of the frangible diaphragm perimeter. The cross-sectional shape of the thickened central portion can be varied, but is preferably lens-shaped as shown in the drawings for molding convenience.

d. The thickest portion of the diaphragm is preferably in the range of about 3 to 10 times the thickness of the diaphragm annulus and frangible rim. This construction provides the desired strength and puncture resistance in the diaphragm center where pestle impact occurs. Excessive thickness is undesirable because the severed diaphragm may then occupy a relatively large part of the capsule interior volume and interfere with efficient intermixing of the amalgam components.

There has been described an inexpensive ready-to-use molded-plastic amalgam capsule which requires no manipulation other than placement in and removal from a vibratory shaker, followed by opening to dispense the amalgam. This simplicity of use is coupled with reliable diaphragm rupture which insures thorough and consistent mixing of the amalgam components in a large-volume chamber to provide a final amalgam of desired and repeatable characteristics. The capsule is also useful in packaging and mix-before-use combining of other multicomponent products such as composite restorative materials, and cements for dental and other applications.

What is claimed is:

1. A multicompartment mixing capsule, comprising:

a hollow central body having a passage therethrough which is closed by an internal barrier diaphragm positioned between first and second ends of the passage, the diaphragm having a thin frangible perimeter integrally formed with the central body, and a thickened center portion which is thereby strengthened against rupture, the diaphragm and thickened center portion being substantially circular, the diaphragm radius being at least about 1.5 times the radius of the thickened center portion;

a first end cap inserted in the first end of the central-body passage to form a first chamber between the first end cap and the diaphragm;

a second end cap inserted in the second end of the central-body passage to form a second chamber between the second end cap and diaphragm; the end caps making an interference fit in the central body, and wherein the diaphragm has a thin annular portion extending between the perimeter and thickened center portion, the annular portion having sufficient elasticity to withstand without breakage radial stresses in the central body arising from insertion of the end caps; and a pestle in one of the chambers to impact against and separate the diaphragm at the perimeter when the capsule is shaken.

2. The capsule defined in claim 1 wherein each end cap is of one-piece integrally molded construction without relatively movable parts.

3. The capsule defined in claim 1 wherein the central body and end caps are made of polyethylene plastic.

4. The capsule defined in claim 1 wherein the diaphragm radius is about twice the radius of the center portion.

5. The capsule defined in claim 1 wherein the diaphragm thickened center portion has a thickness in the range of 3 to 10 times the thickness of the annular portion.

6. The capsule defined in claim 1 wherein the diaphragm annular portion has a thickness in the range of 0.004 inch to 0.012 inch.

7. The capsule defined in claim 6 wherein the diaphragm annular portion has a thickness of about 0.006 inch to 0.007 inch.

8. A self-activating multicompartment amalgam mixing capsule, comprising:

a hollow and integrally molded tubular central body having a bore therethrough which is interrupted by a diaphragm extending across the bore and sealing first and second ends of the bore from each other, the diaphragm having a thin frangible perimeter integrally formed with the body, and a center portion which is strengthened relative to the frangible perimeter by having an increased thickness relative to the perimeter, the diaphragm perimeter and thickened center portion being coaxially circular to define an annular diaphragm portion therebetween, the perimeter radius being at least about 1.5 times the radius of the center portion;

a first end cap fitted in the first end of the body bore to define a first closed chamber between the first end cap and the diaphragm;

a second end cap fitted in the second end of the body bore to define a second closed chamber between the second end cap and the diaphragm;

a pestle in the first chamber;

a first amalgam component in the first chamber; and a second amalgam component in the second chamber; whereby shaking of the capsule causes the pestle to impact against the diaphragm to rupture the diaphragm perimeter to permit intermixing of the amalgam components.

9. The capsule defined in claim 8 wherein the diaphragm center portion has central thickness in the range of about 3 to about 10 times the thickness of the annular portion.

10. The capsule defined in claim 9 wherein the thickness of the annular portion is in the range of about 0.004 inch to 0.012 inch.

11. The capsule defined in claim 10 wherein the thickness of the annular portion is about 0.006 inch to 0.007 inch.

12. The capsule defined in claim 11 wherein the first chamber is axially longer than the second chamber, and wherein the end caps make a snug interference fit in the central body, each end cap being of one-piece integrally molded construction without relatively movable parts.

* * * * *